(12) United States Patent
Chen

(10) Patent No.: US 6,673,105 B1
(45) Date of Patent: Jan. 6, 2004

(54) METAL PROSTHESIS COATED WITH EXPANDABLE EPTFE

(75) Inventor: Yung-Ming Chen, Cupertino, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 87 days.

(21) Appl. No.: 09/825,215

(22) Filed: Apr. 2, 2001

(51) Int. Cl.[7] ................................................. A61F 2/06
(52) U.S. Cl. ...................... 623/1.15; 623/1.13; 623/1.46
(58) Field of Search ........................... 623/1.44, 1.46, 623/1.13, 1.15, 1.32; 427/2.75

(56) References Cited

U.S. PATENT DOCUMENTS

| 5,749,880 | A | * | 5/1998 | Banas et al. |
| 5,788,626 | A | * | 8/1998 | Thompson |
| 5,993,489 | A | * | 11/1999 | Lewis et al. |
| 6,398,803 | B1 | * | 6/2002 | Layne et al. |
| 2001/0021870 | A1 | | 9/2001 | Edwin et al. |
| 2001/0032009 | A1 | | 10/2001 | Layne et al. |
| 2001/0039446 | A1 | | 11/2001 | Edwin et al. |

* cited by examiner

Primary Examiner—Nicholas D. Lucchesi
Assistant Examiner—Lalita M. Hamilton
(74) Attorney, Agent, or Firm—Fulwider Patton Lee & Utecht, LLP

(57) ABSTRACT

A metal prosthesis or metallic stent having a coating of expandable polytetrafluoroethylene (ePTFE) adhered thereto by way of an intermediate laminate containing a primer chemically bonded to the metallic surface over which FEP, a copolymer, is applied.

30 Claims, 3 Drawing Sheets

METAL PROSTHESIS COATED WITH EXPANDABLE EPTFE

BACKGROUND OF THE INVENTION

This invention relates to devices for the treatment of heart disease and particularly to endoarterial prostheses, which are commonly called stents. More particularly, the invention relates to improved metal stents that are coated with expanded polytetrafluoroethylene (ePTFE) in an expandable form.

A focus of recent development work in the treatment of heart disease has been directed to various forms of expandable stents. Stents are generally tube shaped intravascular devices which are placed within a blood vessel to structurally hold open the vessel. The device can be used to maintain the patency of a blood vessel immediately after intravascular treatments and can be used to reduce the likelihood of development of restenosis.

Catheter systems are frequently used to deliver stents to the desired stenotic location. Stents delivered via catheter systems therefore often require extreme flexibility so as to be capable of being transported through varying and tortuous turns and diameters of the vessel pathway prior to arriving at the desired site. Expandable stents are so designed.

Expandable stents are delivered in a collapsed form to the stenotic region and are expanded into the vessel wall thereafter, typically by self expansion properties or by force from an underlying inflated balloon. Most balloon expandable stents can be divided into coil or tubular designs. The tubular stents are usually constructed from a metal tube cut into special pattern, which expands by the force of underlying balloon. The stent typically is crimped on an expandable balloon at the distal end of a catheter assembly by the manufacture or by the operator. After travel in reduced form to the stenotic site, the stent is expanded into the vessel wall by inflating the balloon.

Often referred to as memory stents, self expanding stents may be composed of metals, like nitinol, that are in the elastic or pesudo-elastic range of deformation. Such stents are restrained, typically by a sheath, during travel to the lesion and are sprung open against the vessel wall after the restraint is removed. Since the metal is in its "spring" or "pesudo-elastic" state, it will continue to apply outwardly supportive force to the vessel wall after the stent has been deployed. These stents are available, for example, in mesh designs or, for example, as a chain of corrugated rings.

Stents can also be configured in lesion specific designs, and include a radio-opague marker or coating, and may be in the form of a stent-graft. Stent-grafts are constructed with a prosthetic vascular graft material (eg, e-PTFE or Dacron). The graft material separates the blood flow from the native luminal surface, which may be atherosclerotic, aneurysmal, and/or injured from angioplasty. Grafts have been employed to cover aneurysms, perforations, and degenerated vein graft lesions.

Stents formed from metallic materials are used for strength and rigidity to aid in holding open the targeted vessel wall. Various metals such as stainless steel 316L, tantalum, platinum, nitinol in its martensite form, and alloys formed with cobalt and chromium have often been used to construct such stents whether in self or balloon-expandable form. Metal stents can be formed in a variety of configurations such as helically wound wire stents, wire mesh stents, weaved wire stents, metallic serpentine stents, or in a chain of corrugated rings.

Metallic serpentine stents, for example, not only provide strength and rigidity once implanted they also are designed sufficiently flexible for traveling through the tortuous pathways of the vessel route prior to arrival at the stenotic site. Additionally, such stents can be made expandable by way of expandable balloon, memory after compression, or otherwise.

Stents that possess a metal surface, however, suffer from a number disadvantages. They may possess burrs, nicks, or sharp ends resulting in insertion and travel resistance.

Also, metallic expandable stents, such as wire mesh and serpentine designs, for example, do not possess uniformly solid tubular walls. Although generally cylindrical in overall shape, the walls of such stents are perforated often in more of a framework design of wire-like elements connected together or in a weave design of cross threaded wire. In either case, the perforated design not only provides expandability, it also provides flexibility for traveling to the stenotic site.

Radial expansion of metal stents usually results in expansion of the spaces between the wires or the struts comprising the perforated stent wall. Such enlarged spaces at the stenotic site provide greater openings for ingrowth of thrombotic material that if great enough may lead to invasion of the flow path and result in restriction of fluid flow or even complete blockage. In addition, a stent with such anchoring ingrowth may prove difficult to remove.

Advantages of employing polytetrafluoroethylene (PTFE) as a stent cover material are well known to those skilled in the art. PTFE is a thermoplastic polymer that is chemically inert, is biocompatable, and has a smooth, flexible, and low-resistance surface to aid the stent insertion procedure. Expanded polytetrafluoroethylene (ePTFE) possesses micropores and may be available in an expandable form. The micropores provide mechanical bonding locations for underlying melt thermoplastics and provide openings on the surface of the cover for limited tissue ingrowth and helpful endoluminal anchoring. The expandable form of ePTFE is expandable facilitating expansion of an underlying metal stent.

ePTFE can be made in a variety of thicknesses, but alone can be insufficiently rigid to hold open a vessel. Stents made of only ePTFE would require relatively thick walls and thus relatively small openings for fluid flow. Moreover, ePTFE possesses elastic properties so that expansion of a stent made from only ePTFE may not remain in an expanded condition after an expandable balloon, for example, is deflated and withdrawn. While offering a smooth low friction surface, other stent materials are often preferred for superior structural performance.

The benefits of partial covering and total encapsulation of a stent body with ePTFE material has been recognized. Covered with expandable ePTFE film, a metal stent can be expandable, biocompatible, and can be sufficiently flexible and present a smooth low-friction surface for endoluminal travel. Such a stent may also be sufficiently structurally rigid to support a vessel wall and encourage beneficial microendotheial growth. Additionally, expandable ePTFE as a cover material can provide unbroken cover before, during, and after expansion of the underlying metallic stent body. The integrity of the ePTFE cover can therefore be maintained during stent expansion to continue shielding and protecting the vessel wall from the underlying metal. Additionally, the stent covering of expandable ePTFE serves to protect the patency of the vessel itself by inhibiting thrombotic growth through the large perforations of the expanded metallic stent body.

It is well known, however, that PTFE, ePTFE, and expandable ePTFE, by virtue of their non-stick properties, can not be easily adhered, whether by mechanical bonding, chemical bonding, or otherwise, directly to a surface. Techniques of sodium etching, mechanical roughening, and plasma treating have been proposed in efforts to improve bonding strength between metal and PTFE material. These processes, however, are not practical to cover stents because adhesion of any of the aforementioned forms of PTFE to the metal surface is relatively weak and because such treatment increases the roughness or polarity of the surface which may then cause undesired trauma or cellular response.

For example, twisting, bending, and expansion of the stent body may cause such bonds to break thus loosening or even dislodging the covering from the stent body. Dislodgment of the stent cover while operational could be troublesome.

Rapid growth in the use of endovascular stents suggests improved clinical outcomes with their use. Coronary stents have significantly improved the outcome of percutaneous treatment of coronary stenoses by reducing immediate complications and long-term restenosis. The stent appears to be an advantageous percutaneous device that effectively treats abrupt vessel occlusion by virtue of its ability to support the vessel wall, prevent intimal flap prolapse into the lumen, and prevent elastic recoil of the arterial wall, thus providing an open vessel where laminar blood flow is maintained and the patency of the arterial lumen is preserved.

There has long existed a need for a metallic stent covered with a secure ePTFE cover. There has also long existed a need for a method to bond thermoplastic polymers to a stent with a metal surface. The present invention satisfies this need.

SUMMARY OF THE INVENTION

The invention is directed to an improved stent that has an exterior metal surface which is covered with a primer containing both an active agent for chemical bonding to the metal and a thermoplastic polymer for melting into, and forming a mechanical bond with, a top coating of expandable ePTFE. This invention is also directed to a method for adhering expandable ePTFE to a metal prosthesis.

The improved stent is formed from one or more of a variety of metals including stainless steel, titanium, silver, gold, tantalum, nickel-titanium, manganese, cobalt-chromium, and nickel. Alternatively, the improved stent may be formed with an exterior metal surface from a variety of other materials capable of maintaining its material and mechanical properties after exposure to the temperatures and pressures disclosed herein. Any stent pattern is useable with the present invention coatings.

Applied to the metal surface is a primer containing both a chemically reactive agent for chemical bonding to the metal surface and a thermoplastic polymer for melting into a top coating of thermoplastic polymer. Once applied, the chemically reactive agent of the primer reacts and bonds to the metal surface. The top coating is applied over the primer and the portion of the primer containing the thermoplastic polymer is heated sufficiently to melt forming a mechanical bond with the top coating of expandable ePTFE.

In the event superior adhesion of expandable ePTFE to the stent is desired, the thermoplastic polymer contained in the primer includes fluorinated ethylene propylene (FEP), a copolymer, over which is applied a layer of FEP. Use of primer is necessary as neither FEP nor ePTFE alone adhere adequately to a variety of metals including stainless steel. The over layer of FEP and the primer are then heated to combine with the thermoplastic polymer contained in the primer. The FEP and primer layers are then cooled prior to application of the the ePTFE top coating.

After the expandable ePTFE top coating is applied, the FEP is then heated to above its melting point, but below the melting point of the ePTFE. Not exceeding the melt temperature of the ePTFE preserves the microporous structure and elasticity of the expandable ePTFE coating. With the elevated temperature, pressure is simultaneously applied to the expandable ePTFE to force the melted FEP into the micropores of the expandable ePTFE.

Each of the coatings herein described can be applied by spray, dip, brush-on, plasma deposition, or application of preformed film or any technique known to those skilled in the art. Furthermore, selected portions of the stent may be utilized, for example, for application of one or more of the coatings. In one embodiment, for example, only the annular ring ends of the stent are coated with primer and FEP, and a preformed sleeve of expandable ePTFE is pulled or rolled over the stent body and adhered thereto by application of heat and pressure. Adherence to only the ends of the stent body can provide an outer covering of expandable ePTFE without adherence of the ePTFE to the entire outer surface of the stent body. The unadhered expandable ePTFE film, while not bonded to the stent body, is free to be physically supported by, and expanded in conformance with, the underlying metal stent body.

In another embodiment, expandable ePTFE films encapsulate the entire stent body by bonding inner and outer sleeves of expandable ePTFE to the stent body to wholly cover the stent sealing the metal from exposure to any body fluid or tissue. In yet another embodiment, all surfaces of the stent body, including the surfaces between interstitial gaps in the stent wall, are coated by a covering of primer, FEP, and expandable ePTFE.

In addition, multiple layers of primer, FEP and expandable ePTFE may be applied as desired to achieve desired coating thickness. Expandable ePTFE is preferred for its microporus and expandable properties. Where expansion is not required, ePTFE may be substituted. Where neither expansion nor a superior bond is required PTFE may be substituted. In addition, other melt thermoplastic polymers may be used in lieu of FEP and expandable ePTFE depending upon the performance desired. Furthermore, an ePTFE cover may be adhered to a stent or, similarly, to a medical prosthesis with a metallic surface. Attaching a film of ePTFE in the form of a graft to a metal stent by adhesion as disclosed is also within the scope of the invention.

Other features and advantages of the invention will become apparent from the following detailed description, taken in conjunction with the accompanying drawings, which illustrate, by way of example, the features of the invention.

DETAILED DESCRIPTION OF THE PREFERRED EMBODIMENTS

Expandable metallic stents are well known to those in the art. There exists a wide variety of stent configurations for implanting in human vessels. Perforated metal stents, for example, have been widely utilized. Although utilitarian in providing rigidity, resistence to crushing, and durability, perforated metal stents are often also expandable in vivo. Expansion of the stent usually results in the enlargement of the perforations in the stent walls. Without a barrier, these enlarged perforations, however, provide openings for tissue ingrowth into the fluid flow path. Substantial tissue ingrowth may result in partial or total occlusion of the fluid pathway and increase the difficulty of removing the occlusion.

Figure 1:
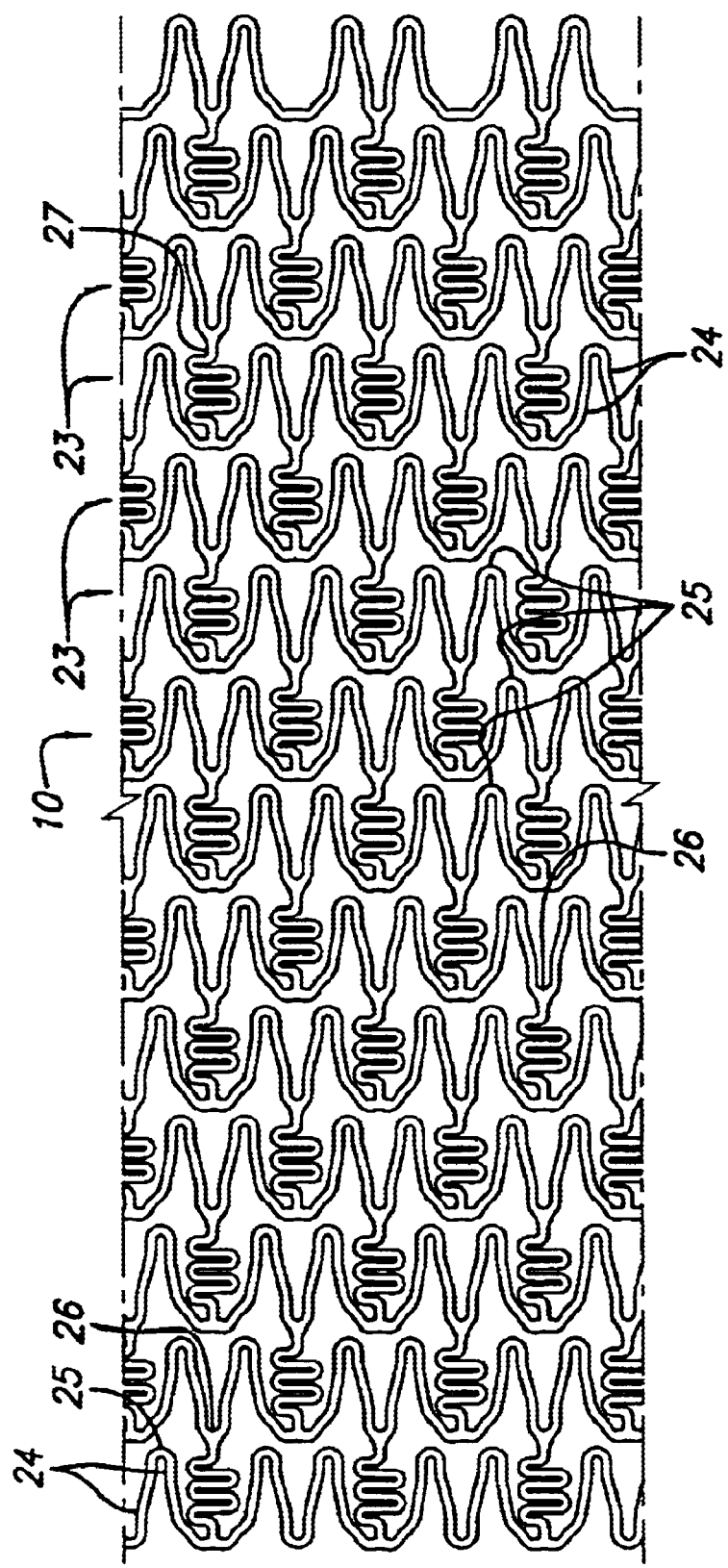
FIG. 1 is a plan view of a metal stent body of the present invention laid flat.

Referring to FIG. 1, the stent body 10 of the present invention is one of expandable form although a non-expandable stent may be employed. FIG. 1 illustrates a flattened metal stent body 10 of serpentine pattern that includes a plurality of cylindrical elements 23 of undulating peaks 25 and valleys 26 connected together by transitional elements 24. Each cylindrical element 23 is connected by way of interconnecting links 27. The length of the stent body of the present embodiment is determined by the length of the peaks, valleys, transitional elements, interconnecting links, and the number of cylindrical elements connected together. The stent body can be made from a variety of metals including but not limited to gold, silver, nickel-titanium, titanium, tantalum, stainless steel, and cobalt-chromium. Manufacture of such stent bodies is known to those in the art.

Figure 2:
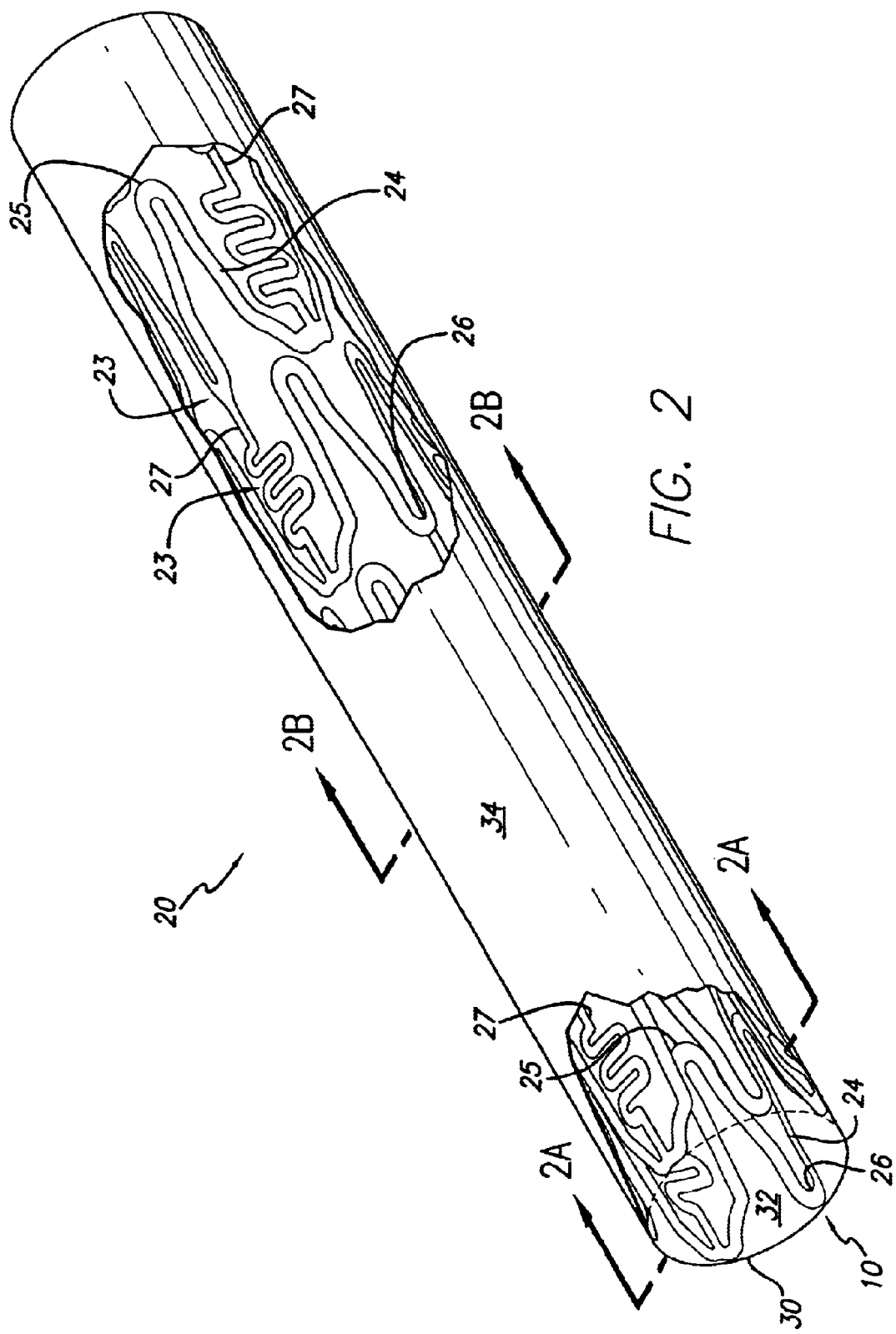
FIG. 2 is a perspective view of the stent body shown in FIG. 1 formed into a tubular metal stent body encased in a partially broken away tubular sleeve of expandable ePTFE according to the present invention.

FIG. 2 illustrates a stent 20 of the present invention that includes a tubular expandable metal stent body 10 of serpentine design consisting of cylindrical elements 23, of peaks 25, valleys 26, and transitional elements 24. The cylindrical elements are connected together by one or more connecting links 27 between adjacent cylindrical elements. Expandable metal stents, like the present invention, have an outer diameter of about 1.5 mm in the unexpanded condition, and can be expanded to an outer diameter of 4.5 mm or more for coronary applications, and much larger for other applications (e.g., peripheral or biliary). Typical wall thickness of an expandable stent is about 0.10 mm. The stent body of the present embodiment is comprised of metal, however, a stent body having a metallic exterior surface may also be utilized.

The tubular stent body in the subject embodiment is in the unexpanded state within a top coating of expandable ePTFE in the form of a pre-formed tubular sleeve 30 of expandable ePTFE film having an inner surface 32 and an outer surface 34. The sleeve of expandable ePTFE film is expandable to conform, once adhered to the stent body, to the underlying stent body during travel to the stenotic site. In addition, the expandable ePTFE material is capable of providing unbroken cover during and after radial expansion of the underlying stent body to its permanently deployed form. Manufacture of expandable ePTFE film in the form of a tubular sleeve will be known to those in the art.

Figure 2A:
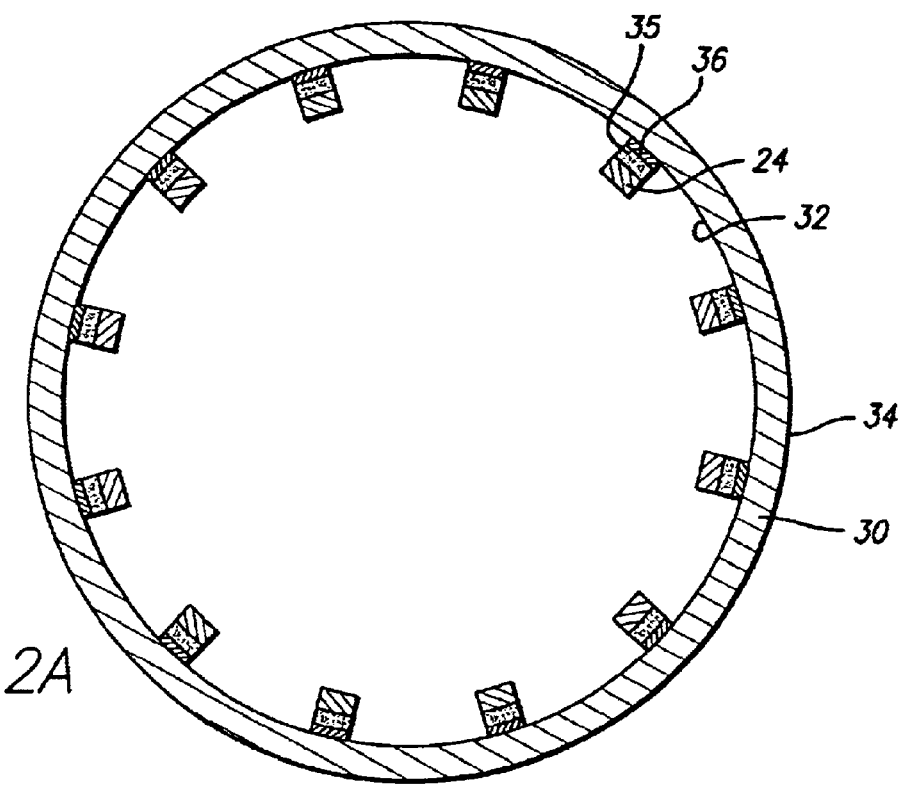
FIG. 2A is an enlarged transverse cross-sectional view taken along line 2A—2A of FIG. 2.

Referring to FIG. 2A telescoped in concentric relationship over the tubular stent is a tubular sleeve 30 of expandable ePTFE. The ePTFE sleeve has a circumferential inner surface 32 and a circumferential outer surface 34. The inner surface of the sleeve is adhered to the transitional elements 24 by way of application of a primer layer 35 over which is applied a layer of fluorinated ethylene propylene (FEP) 36. After application of the primer and FEP layers in the present embodiment, the sleeve is positioned over the stent body and the FEP is melted and forced by application of pressure into the inner surface of the sleeve forming a mechanical bond between the sleeve and the FEP.

The primer layer 35 when applied must include a chemically active component to chemically react with the metallic surface of the transitional elements 24 and to form a chemical bond between the primer and the metal of the stent body. Dupont 850-300/VM7799, for example, contains chromic and phosphoric acid which, when exposed to high temperature, will react to form such a bond. The primer will also preferably include FEP, but may include PTFE, perfluoroalkoxy (PFA), or other melt thermoplastic polymer which, when applied and heated as part of the primer, will be will be available for subsequent mechanical bonding to a separate over layer of FEP 36 or to a top coating of ePTFE 30. A mixing of the thermoplastics together may also occur should they be melted, and may include chemical bonding such as with Van der Walls forces. An acceptable weight ratio of active component to polymer is between 80 percent active component to 20 percent polymer to between 60 percent active component to 40 percent polymer.

In the present embodiment, the primer layer 35 is applied to the end of the stent body. In other embodiments it may be desirable to coat a different portion of the stent body. The primer may be sprayed, dipped, brushed, or plasma deposited onto the metal stent body to achieve a thickness of between 0.010 and 0.050 mm, preferably 0.025 mm. Once applied, a primer such as Dupont 850-300/VM7799, for example, requires heat to form sufficient chemical bonding with the metal surface of the stent body. Heating may be accomplished by inductive, resistive, or other means of heating known to those in the art to a temperature of between 500° Fahrenheit and 700° Fahrenheit for a period of 1 to 30 minutes at standard atmospheric pressure. The heat is then removed and the primer is allowed to cool and solidify.

In the current embodiment, an intermediate FEP layer 36, such as DuPont 850-200 clear, is applied over the primer layer 35. The FEP layer can be sprayed, dipped, brushed on, over the primer layer to a thickness of between 0.025 and 0.130 mm thick, preferably 0.025 mm. The FEP layer can be applied over the primer layer by plasma deposition, but the DuPont 850-200 clear is not suitable for this process so another FEP compound would be used. The primer and FEP layers are then heated to a temperature of between 550° Fahrenheit and 620° Fahrenheit for a period of 1 to 30 minutes at standard atmospheric pressure so that both the FEP layer and polymer contained in the primer layer may melt to form an adhering mechanical bond. The heat is then removed and the FEP is allowed to cool and solidify.

In the present embodiment, the pre-formed tubular sleeve 30 of ePTFE of 0.025 to 0.260 mm, preferably 0.076 mm thickness, is then applied over the FEP layer 36. This can be accomplished, for example, by sliding or rolling the sleeve over the stent body. Once the sleeve is positioned over the stent body the temperature is raised by heating to between 550° Fahrenheit and 620° Fahrenheit for a period of 5 to 60 seconds at a pressure of between 5 psi and 50 psi. As the melting point of FEP is lower than that of ePTFE, this temperature is sufficient to melt the underlying FEP, but is not so hot as to substantially melt the top coating of expandable ePTFE film. The melting of ePTFE for a prolonged period of time may substantially change its crystalline structure and alter its properties including its micropores. Although not required for some level of bonding to the ePTFE, the simultaneous application of pressure with heat forces the melted FEP into superior mechanical bonding contact with the surface and micropores of the ePTFE. The ePTFE film may tear if pressure in excess of 50 psi is applied.

Figure 2B:
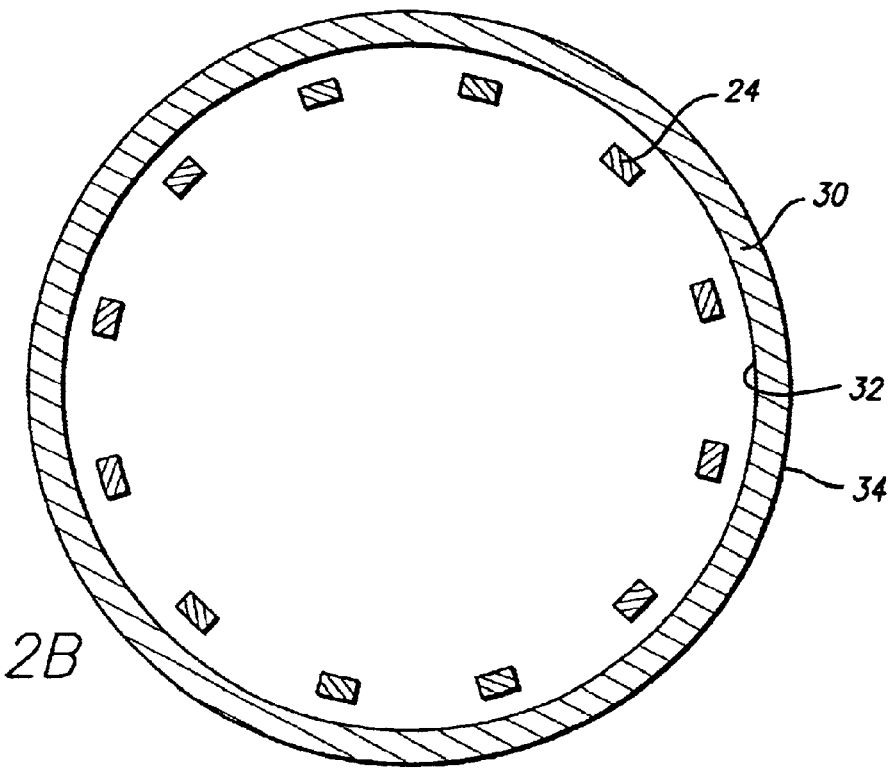
FIG. 2B is an enlarged transverse cross-sectional view taken along line 2B—2B of FIG. 2.

Referring to FIG. 2B, the medial portion of the tubular expandable ePTFE sleeve 30 is not adhered on the inner surface 32 to the stent body. This disconnection of the sleeve at the intermediate length of the stent body leaves the two components free to move somewhat relative to one another, as shown in FIG. 2A, thus enhancing the flexibility and uniformity of expansion adjacent the end of the stent body.

Application of ePTFE is not limited to the form of a pre-formed tubular sleeve 30. For example, a film of ePTFE can be rolled into a tubular sleeve. The primer for ePTFE material may also be applied in the form of spray, dip, brush-on, or plasma deposited coating and adhered to a metal surface such as a stent body, other forms of medical prostheses, or to any other metallic surface such as a wire, for example, before or after the wire is formed into the shape of a stent or other medical device.

In another embodiment, the primer layer, including FEP, is adhered to a metal stent body over which a layer of FEP is applied. However, it is only after both the FEP-containing primer layer and the FEP over layer are applied to the stent body that the primer layer is heated sufficiently to react with the metal surface and to melt the FEP. The primer and FEP layers are then heated to a temperature of between 550° Fahrenheit and 620° Fahrenheit for a period of 1 to 30 minutes at standard atmospheric pressure so that a melting of the FEP layer and polymer contained in the primer layer may melt together to form an adhering mechanical bond. The heat is then removed and the FEP is allowed to cool and solidify before application of the top coating of ePTFE.

As will be appreciated by those skilled in the art, the method of fabricating the stent has broad applications. This method may be employed for treating numerous different metallic implant devices. The method may be employed to treat a medical prosthesis having an exterior metallic surface by applying a primer including a chemically reactive agent, to facilitate chemical bonding of the primer to the metallic surface, and a thermoplastic polymer to facilitate mechanical bonding to a top coating including ePTFE, heating the primer layer to chemically bond it to the surface, applying a top coating including ePTFE to the primer, and heating the thermoplastic contained in the primer layer to bond with the ePTFE coating. Also disclosed herein is a method to apply a layer containing FEP between the primer layer and the top coating of ePTFE.

The present invention satisfies a great need for a metal stent with a secure and expandable ePTFE cover. Adherence of ePTFE to a stent body, through the use of a chemically reactive primer, however, has not been heretofore disclosed. Additionally, the present invention satisfies the need for a method to fabricate such a stent. The benefits of the present invention are many to those in the art with a need for improved adhesion of ePTFE to the metal surface of a medical prosthesis.

An expandable metal stent can be formed to possess a low-insertion profile, flexibility for traveling the tortuous pathway to the stenotic site, and a structurally strong framework after expansion to hold open the vessel at the targeted site. A stent covered with a secure coating of expandable ePTFE further provides a smooth low-friction surface to aid in the insertion procedure, is biocompatible, and is expandable to provide unbroken cover before, during, and after expansion of the underlying stent body. The integrity of the expandable ePTFE cover can therefore be maintained during stent expansion and continue, after expansion, shielding and protecting the vessel wall from the underlying metal. In other words, a stent covered with expandable ePTFE serves to protect the patency of the vessel since the perforations in the stent are covered so by the material so that plaque does not push through (prolapse) the perforations into the vessel. Furthermore, the micropores contained within the ePTFE provide small openings facilitating beneficial microendothelial tissue ingrowth that serves to anchor the ePTFE film to the vessel wall. During the formation of the present invention, the micropores also facilitate improved mechanical bonding to the FEP applied prior to the ePTFE top coating.

The embodiments heretofore discussed are in no way intended to limit the scope of the invention. Various changes and improvements may also be made to the invention without departing from the scope thereof.

What is claimed is:

1. A device for use in treating a body lumen, comprising:
   a tubular body having a metallic exterior and interior surface and openings formed therein;
   a primer to facilitate bonding of at least a portion of an inner surface of an ePTFE sleeve adhered to the metallic exterior surface;
   a single layer of coating including ePTFE adhered to the primer;
   wherein the primer and the single layer of coating are adhered to the tubular body metallic exterior surface such that the metallic interior surface is left exposed.

2. The device of claim 1, wherein the primer is chemically bonded to the exterior surface.

3. The device of claim 1, wherein the primer includes FEP.

4. The device of claim 1, wherein the ePTFE is expandable.

5. The device of claim 1, wherein the interior metallic surface is devoid of adhesive material.

6. A device for use in treating a body lumen, comprising:
   a tubular body having a metallic exterior and interior surface and openings formed therein;
   a primer being chemically bonded to the exterior surface, the primer including FEP to facilitate bonding to expandable ePTFE;
   a single layer of coating consisting of expandable ePTFE adhered to the primer;
   wherein the primer and the single layer of coating are bonded and adhered to the tubular body metallic exterior surface such that the metallic interior surface is left exposed.

7. A device for use in treating a body lumen, comprising:
   a prosthesis having an exterior and an interior metallic surface;
   a primer to facilitate bonding of a thermoplastic polymer adhered to the exterior metallic surface;
   a single layer of coating including a thermoplastic polymer adhered to the primer;
   wherein the primer and the single layer of coating are adhered to the prosthesis metallic exterior surface such that the metallic interior surface is left exposed.

8. The device of claim 7, wherein the primer is chemically bonded to the exterior surface.

9. The device of claim 7, wherein the primer includes FEP.

10. The device of claim 7, wherein the single layer of coating includes ePTFE adhered to the prosthesis metallic exterior surface in an even manner.

11. The device of claim 7, wherein the coating includes expandable ePTFE.

12. The device of claim 11, wherein the coating is mechanically bonded to the expandable ePTFE.

13. A method of making a device for use in treating a body lumen, comprising:

providing a prosthesis having an exterior and an interior metallic surface;

applying a primer layer to the exterior metallic surface in a manner such that the interior metallic surface is left exposed, the primer including a chemically reactive agent to facilitate chemical bonding of the primer to the exterior metallic surface and a thermoplastic polymer to facilitate mechanical bonding to a single layer of coating of ePTFE;

heating the primer to chemically bond the chemically reactive agent to the exterior metallic surface;

applying a the single layer of coating including ePTFE to the primer; and heating the primer to chemically bond the thermoplastic polymer to the ePTFE coating.

14. The method according to claim 13, wherein the primer is chemically bonded to the exterior surface.

15. The method according to claim 13, wherein the primer includes FEP.

16. The method according to claim 13, wherein the PTFE is in the form of ePTFE.

17. The method according to claim 13, wherein the PTFE is in the form of expandable ePTFE.

18. The method according to claim 13, wherein the coating is subjected to pressure to enhance bonding to the primer.

19. A method of making a device for use in treating a body lumen, comprising:

providing a medical prosthesis having an exterior and an interior metallic surface;

applying a primer to the exterior metallic surface in a manner such that the interior metallic surface is left exposed, the primer including a chemically reactive agent to facilitate chemical bonding of the primer to the exterior metallic surface and a thermoplastic polymer to facilitate mechanical bonding to an over layer including FEP;

applying the over layer including FEP over the primer to facilitate mechanical bonding to a single layer of coating including ePTFE; and applying the single layer of coating including ePTFE over the over layer.

20. The method according to claim 19, wherein the primer is chemically bonded to the exterior metallic surface.

21. The method according to claim 19, wherein the primer is heated to chemically bond to the exterior surface.

22. The method according to claim 19, wherein the primer includes FEP.

23. The method according to claim 22, wherein the primer is heated to mechanically bond with the over layer.

24. The method according to claim 22, wherein the over layer is heated to mechanically bond with the coating.

25. The method according to claim 24, wherein the coating is subjected to pressure to enhance mechanical bonding to the over layer.

26. The method according to claim 19, wherein the coating includes ePTFE.

27. The method according to claim 19, wherein the coating includes expandable ePTFE.

28. A method of making a device for use in treating a body lumen, comprising:

providing a medical prosthesis having an exterior and an interior metallic surface;

applying a primer to the exterior metallic surface in a manner such that the interior metallic surface is left exposed, the primer including a chemically reactive agent to facilitate chemical bonding of the primer to the exterior metallic surface and FEP to facilitate mechanical bonding to an over layer including FEP;

heating the primer to facilitate chemical reaction with the exterior metallic surface;

applying the over layer including FEP over the primer to facilitate mechanical bonding to a single layer of coating including ePTFE;

heating the over layer and the primer to facilitate mechanical bonding of the over layer to the primer;

applying the single layer of coating including expandable ePTFE over the over layer;

heating the over layer to facilitate mechanical bonding of the over layer to the single layer of coating; and applying pressure to the single layer of coating to enhance mechanical bonding of the over layer to the coating.

29. A method of making a device for use in treating a body lumen, comprising:

providing a prosthesis having an exterior and an interior metallic surface;

applying a primer layer to the exterior metallic surface in a manner such that the interior metallic surface is left exposed, the primer including a chemically reactive agent to facilitate chemical bonding of the primer to the exterior metallic surface and a thermoplastic polymer to facilitate mechanical bonding to a single layer of coating of ePTFE;

heating the primer to chemically bond the chemically reactive agent to the exterior metallic surface;

applying the single layer of coating including ePTFE to the primer in an even manner; and heating the primer to chemically bond the thermoplastic polymer to the ePTFE coating to cause the thermoplastic polymer to extend from the primer into the single layer of coating including the ePTFE.

30. The method according to claim 29, wherein the coating is applied over the primer and the portion of the primer containing the thermoplastic polymer is heated sufficiently to melt thereby forming a mechanical bond with the coating of the ePTFE.

* * * * *

UNITED STATES PATENT AND TRADEMARK OFFICE
CERTIFICATE OF CORRECTION

PATENT NO. : 6,673,105 B1
DATED : January 6, 2004
INVENTOR(S) : Yung-Ming Chen

It is certified that error appears in the above-identified patent and that said Letters Patent is hereby corrected as shown below:

Column 9,
Line 15, after "applying" delete "a".

Signed and Sealed this

Twenty-fifth Day of May, 2004

JON W. DUDAS
*Acting Director of the United States Patent and Trademark Office*